US00PP13470P3

(12) United States Plant Patent
Strickland

(10) Patent No.: US PP13,470 P3
(45) Date of Patent: Jan. 14, 2003

(54) OVERCUP OAK TREE NAMED 'QLFTB'

(75) Inventor: Thomas Julian Strickland, Statesboro, GA (US)

(73) Assignee: Tree Introductions, Inc., Bishop, GA (US)

( * ) Notice: Subject to any disclaimer, the term of this patent is extended or adjusted under 35 U.S.C. 154(b) by 0 days.

(21) Appl. No.: 09/877,854

(22) Filed: Jun. 7, 2001

(65) Prior Publication Data

US 2002/0188974 P1 Dec. 12, 2002

(51) Int. Cl.[7] ..... A01H 5/00

(52) U.S. Cl. ..... Plt./225

(58) Field of Search ..... Plt./225

*Primary Examiner*—Bruce R. Campell
*Assistant Examiner*—A Para
(74) *Attorney, Agent, or Firm*—Klarquist Sparkman LLP

(57) ABSTRACT

A Overcup Oak tree named 'QLFTB' having dense, upright, uniform branching habit, yellow-orange-red fall color, and fast growth rate and also which is capable of being reproduced reliably using vegetative cuttings.

7 Drawing Sheets

LATIN NAME OF GENUS AND SPECIES

*Quercus Iyrata* 'QLFTB'.

DESCRIPTION

The present invention relates to a new and distinct variety of *Quercus Iyrata*, Overcup Oak, which has been given the varietal name 'QLFTB.' I discovered my new tree in 1996 as a chance seedling of unknown parentage growing in a cultivated area in Statesboro, Ga.

The seeds were collected from a single tree in Athens, Ga. The seeds were collected in the fall of 1991 and planted into seedbeds in late winter of 1992. In the spring of 1993, bare-root liners were transplanted to a nursery field. In January of 1998, my new tree was moved to an observation site in Oconee County, Ga., where it has remained since that time. It is now about eight and one half years old from a seed.

As I observed the initially discovered tree of my new variety, the uniqueness of this tree became apparent because of a dense, upright, uniform branching habit, yellow-orange-red fall color, and fast growth rate as compared to a typical seedling. It was observed that my new tree grew approximately 30% faster than most of the other Overcup Oak Trees in the field that were planted from the same seed source. These characteristics distinguish my new tree from other typical Overcup Oaks known to me.

In 1996, this new tree was successfully propagated by vegetative cuttings at my direction, and the progeny have thus far proven to retain the dense, upright, uniform branching habit, fall color, and fast growth rate of the initially discovered tree even as smaller plants. Asexual reproduction of my new plant has taken place in Bulloch County, Ga.

I observed this tree of my new variety for a period of time and believe it is particularly useful as a street tree and for use on commercial sites where growing conditions are difficult, particularly areas that may be wet for a portion having the year. My new oak tree can also be used on golf courses, parks, and other areas where a tree having these characteristics is needed. Its fast growth rate offers growers an accelerated finished product over a typical seedling, allowing for a quicker crop rotation.

Cultivated Overcup Oak trees, insofar as I am aware, are represented in the industry solely by seedling material. Although Overcup Oak trees are more consistent from seed than many other oaks, there is still a degree of variance in both the landscape and in nurseries. Seedling Overcup Oak trees can be variable in growth rate, habit, and fall color. My new tree has a dense, upright, uniform branching habit, better fall color, and a faster growth rate in comparison to other varieties of Overcup Oak trees of which I am aware.

Overcup Oak trees in youth are typically pyramidal-oval and oval-rounded to rounded in habit at maturity. On average these tree reach 40' to 60' high and wide. However, the national champion is 156' tall by 120' wide. Overcup Oak trees are native to bottomlands where it is found in sloughs and backwater areas from New Jersey to Florida, west to Missouri and Texas. Overcup Oak trees perform best in acid soils, and do well in the heat, drought, and humidity of the Southeast. These trees also do well in the lower temperatures and high precipitation of the East and Mid-Atlantic as well as the more arid Midwest. Overcup Oak trees are known to be hardy in USDA Zones 5–9. Overcup Oak trees are relatively easy to transplant because of a superior root system compared to other oaks.

My new variety has been asexually propagated by vegetative cuttings at my direction. This propagation and observation of the resulting progeny have proven the unique combination of characteristics of my new variety to be firmly fixed and reproduce true to type. Furthermore, these observations have confirmed that my new variety represents a new and improved variety of Overcup Oak tree as particularly evidenced by the dense, upright uniform branching habit, fall color, and fast growth rate and which can reliably be asexually propagated using vegetative propagation techniques.

The accompanying photographs depict the color of the tree and foliage of my new variety as nearly as is reasonably possible to make the same in a color illustration of this character.

My new 'QLFTB' variety of Overcup Oak tree is currently growing at an observation site in Oconee County, Ga. It is located in an area of Oconee County that has a clay loam soil type. Oconee County is in USDA Hardiness Zone 7 and receives an average rainfall of 50 inches each year, although actual rainfall in any given year can typically range between 30 and 60 inches. The hardiness of my new variety has yet to be determined.

The following is a detailed description of my new variety of Overcup Oak tree with color terminology in accordance with The Royal Horticultural Society (R.H.S.) Colour Chart published by The Royal Horticultural Society of London. The observations are of the initially discovered tree growing at the observation site in Oconee County, Ga. My new tree has not been observed under all growing conditions and thus variations may occur as a result of different growing conditions.

My new variety of Overcup Oak tree is characterized by a dense, upright, uniform branching habit, yellow-orange-red fall color, and a fast growth rate (FIGS. 1, 2, 5, and 7). The initially discovered tree is currently 9.75 inches in caliper at 12 inches above the ground after eight and one half years. The initially discovered tree is currently 24 feet high and 16 feet wide with a height to width ration of 1.5.

Figure 6:
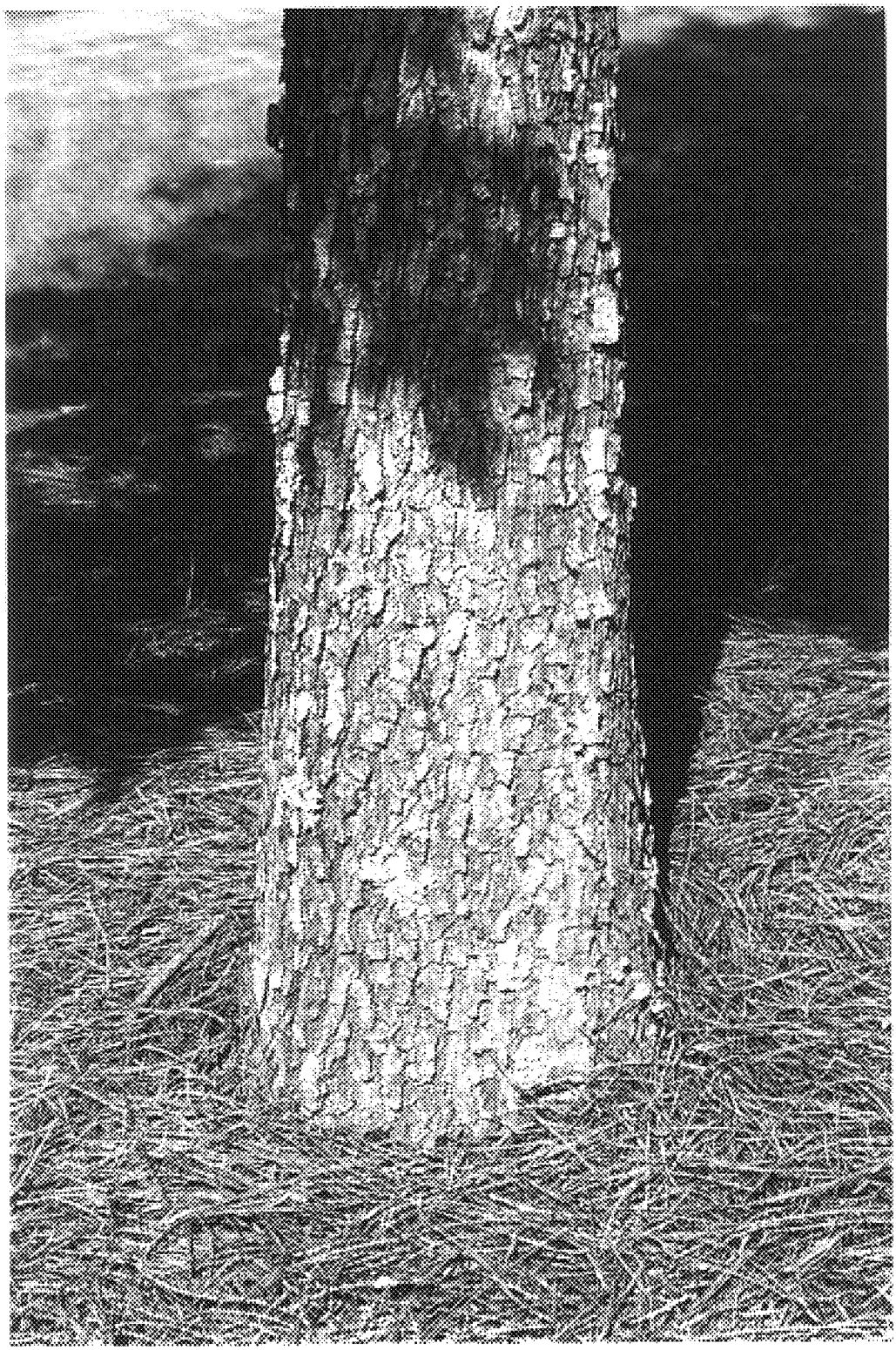
FIG. 6 is a close up of the trunk of the initially discovered tree.

The bark of my new tree is typical of the species, being smooth to slightly rough and gray-brown on young trees, and becoming gray to gray-green and scaly at maturity (FIG. 6), reminiscent of *Quercus alba*. However, it is not quite as scaly as a typical *Quercus alba*. The color of the mature bark is also typical of the species, with the color being shown in FIG. 6, light gray-green (RHS 188C) with patches of light green-white (RHS 157C).

Figure 1:
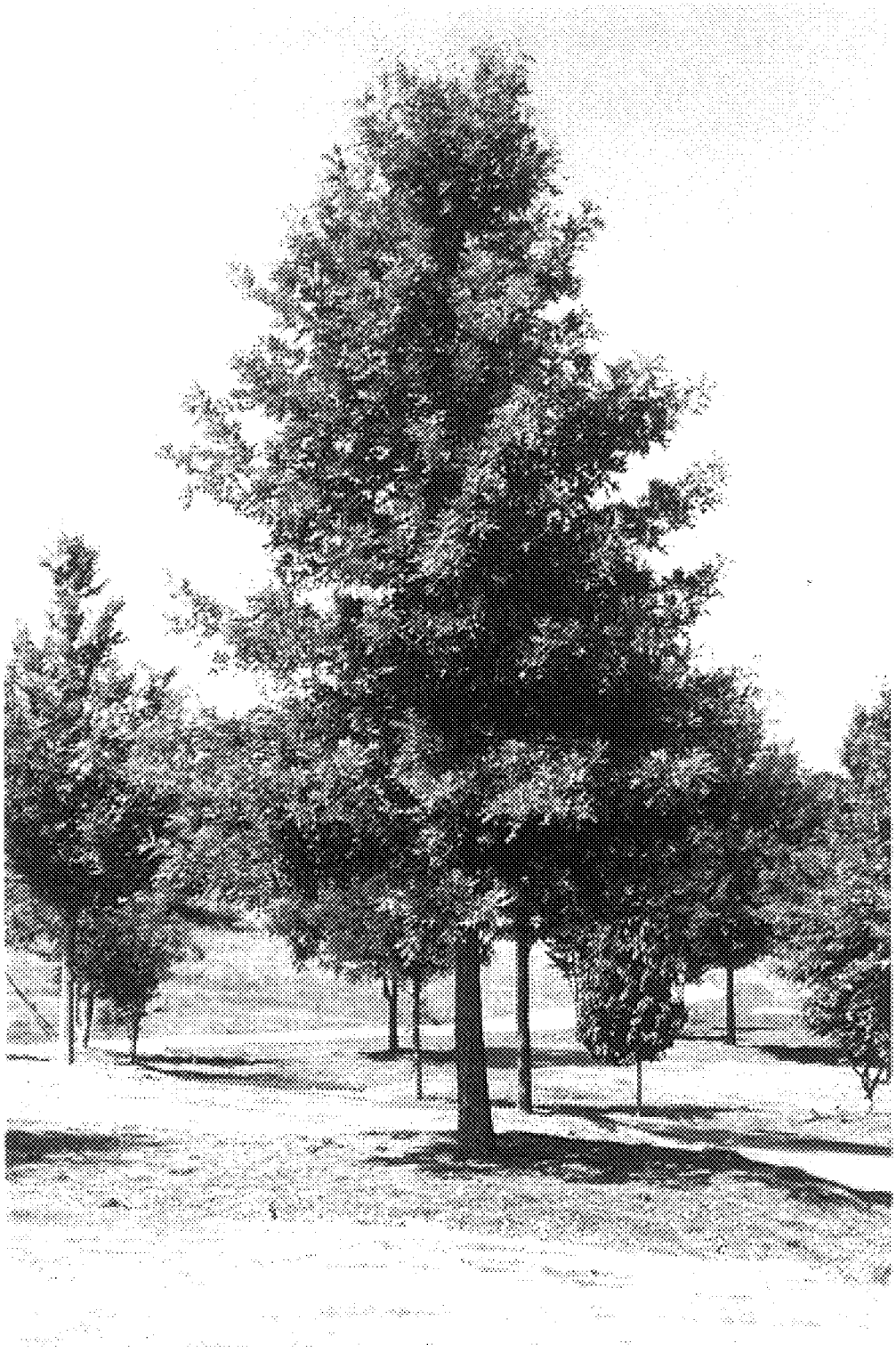
FIG. 1 is a photograph of the initially discovered tree of my new variety in summer leaf.
Figure 2:
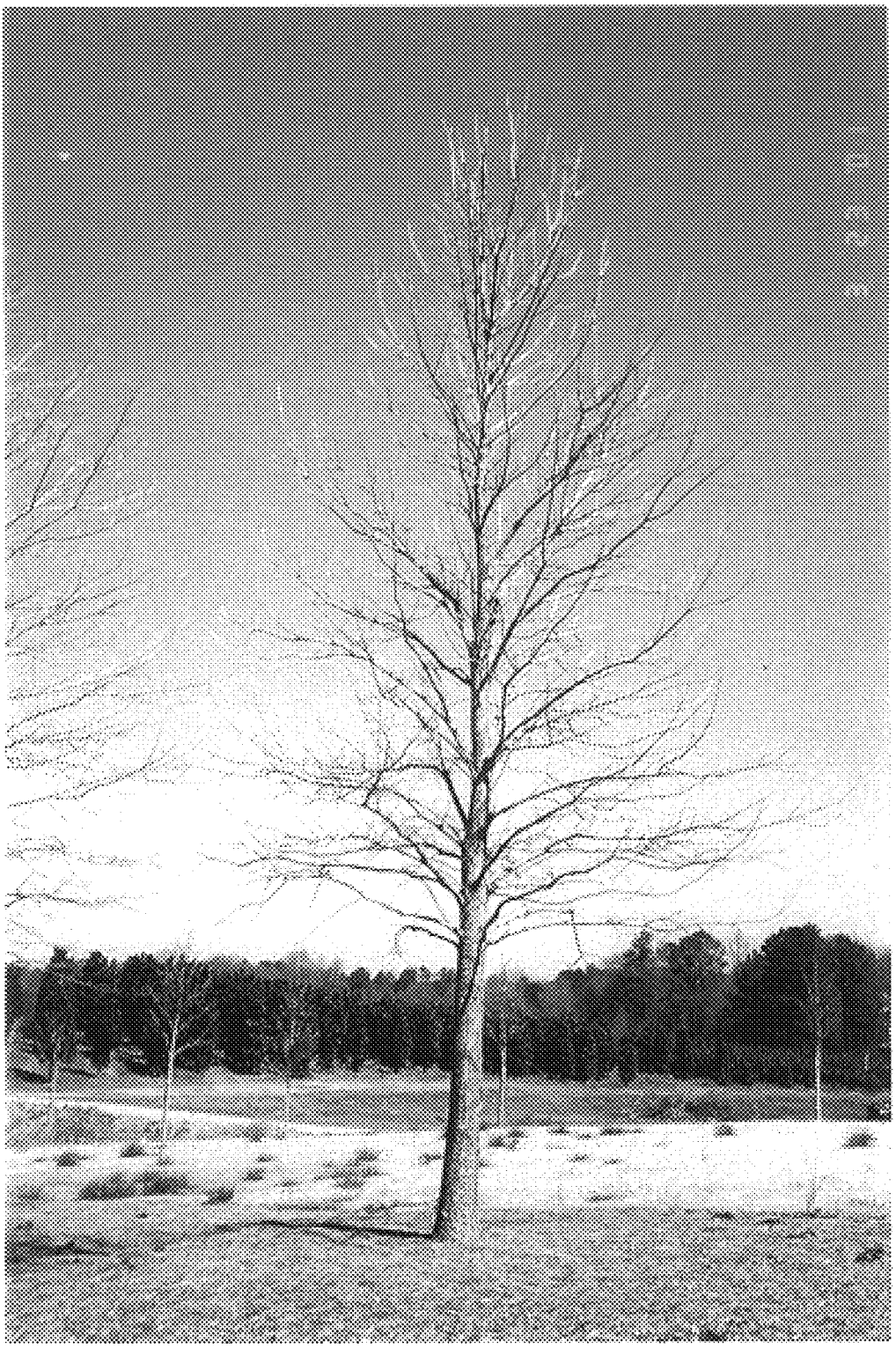
FIG. 2 is a photograph of the initially discovered tree of my new variety during winter.
Figure 7:
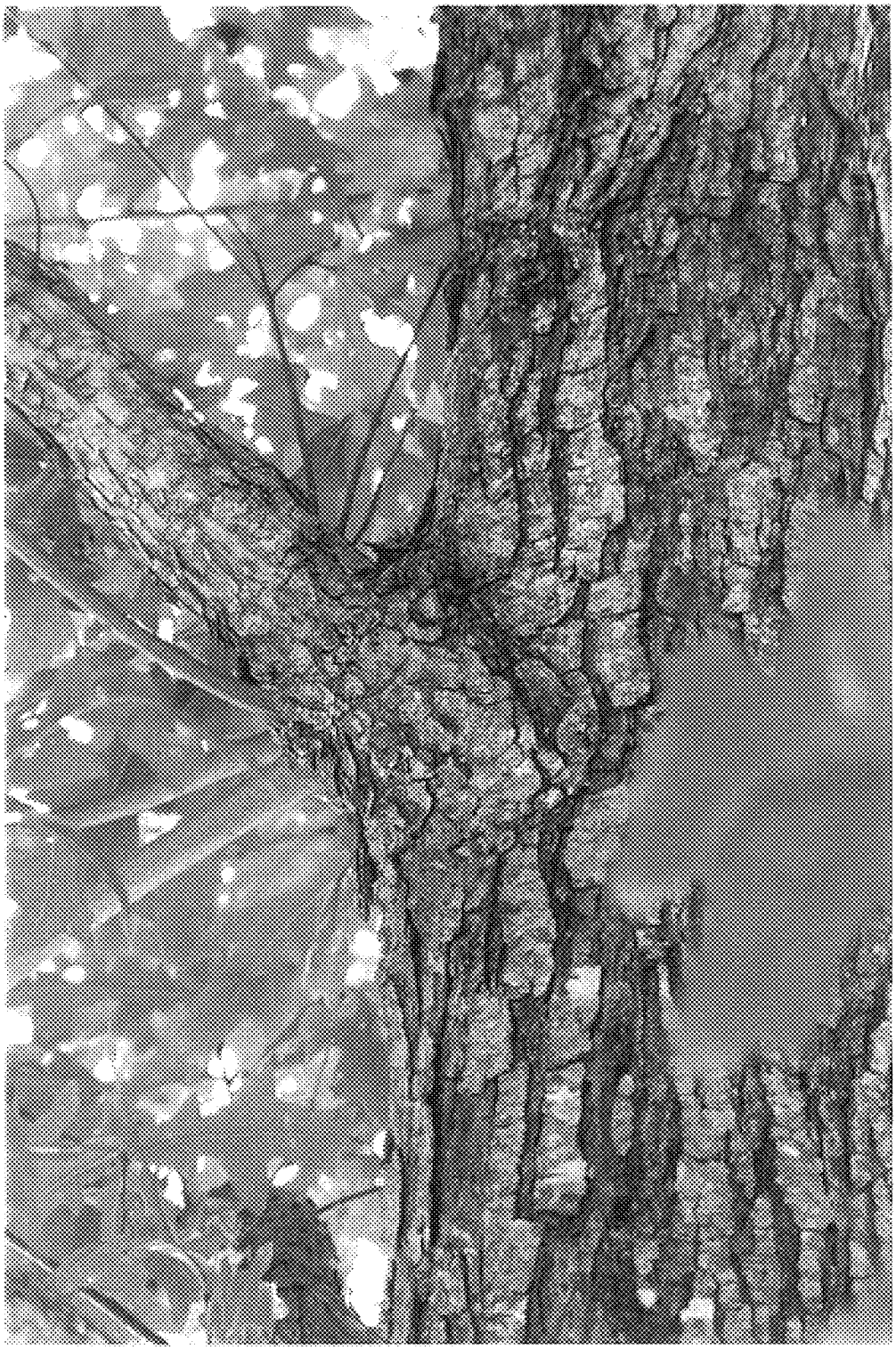
FIG. 7 is a close up of the typical branching habit of my new variety.

The branching habit of my new tree is upright pyramidal-oval. Branches at the base of the tree typically emerge at about 80 degree angles to the trunk. Branches at the top of the tree typically emerge at about a 50 degree angle to the leader and tend to flatten with age (FIGS. 1, 2, and 7).

Figure 3:
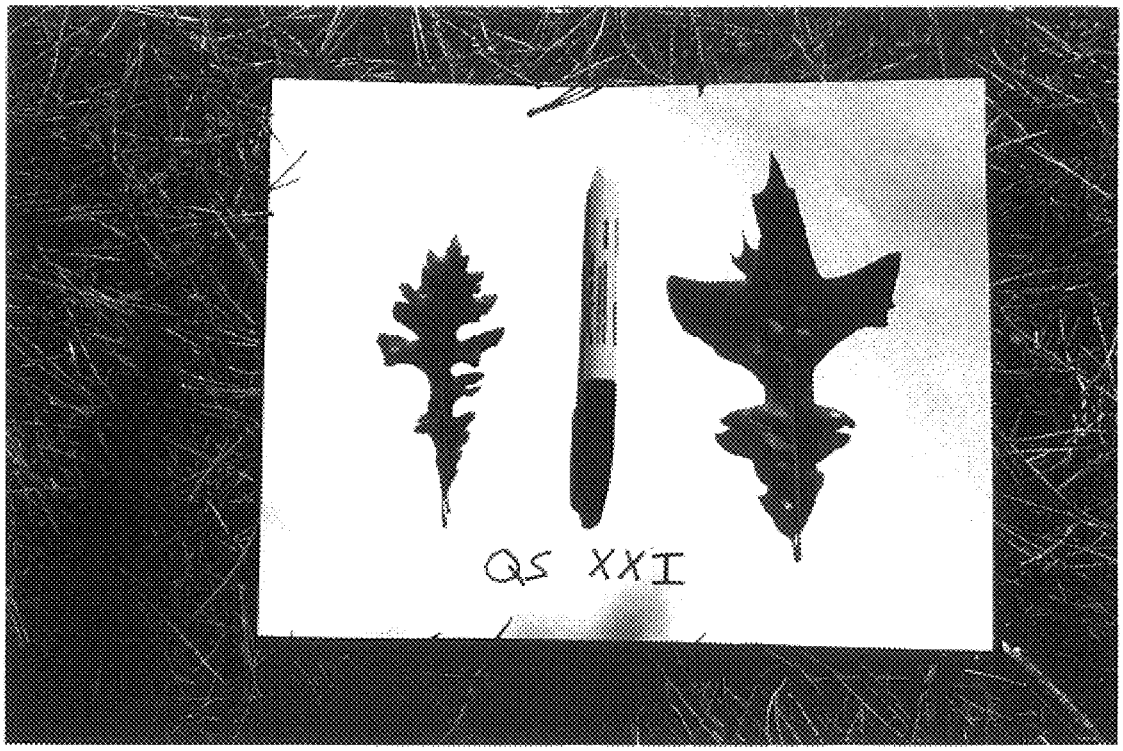
FIG. 3 is a close up of the upper side of two single leaves from a tree of my new variety.
Figure 4:
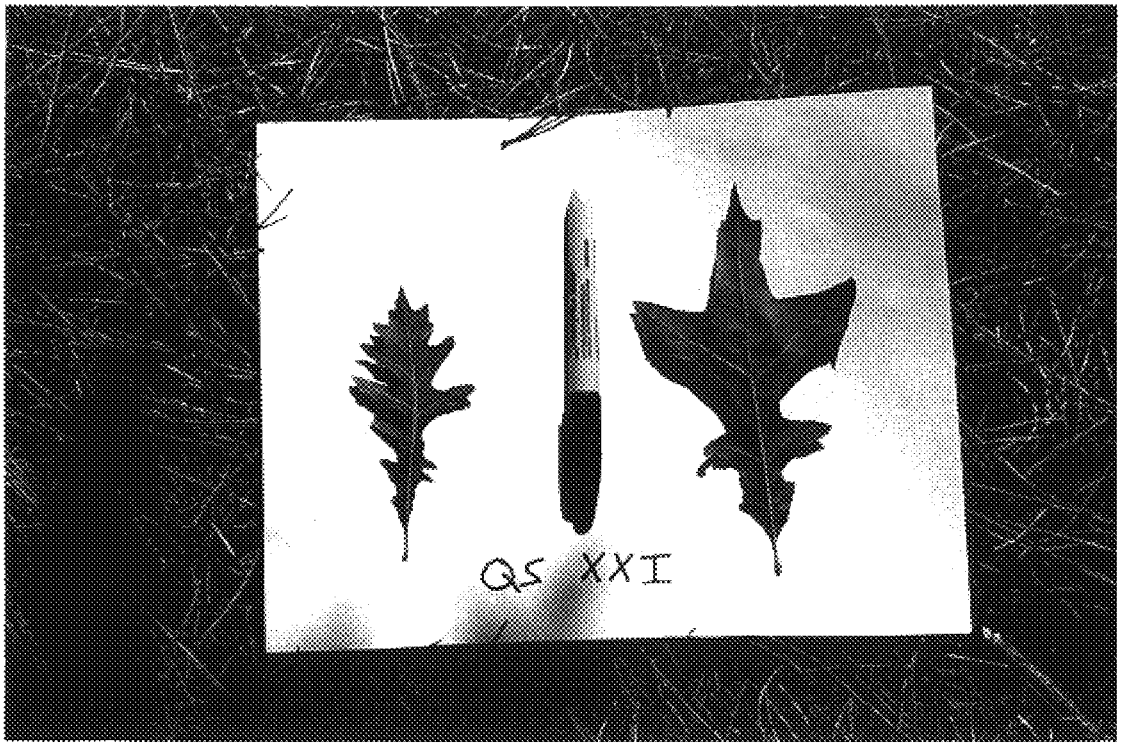
FIG. 4 is a close up of the under side of two single leaves from a tree of my new variety.
Figure 5:
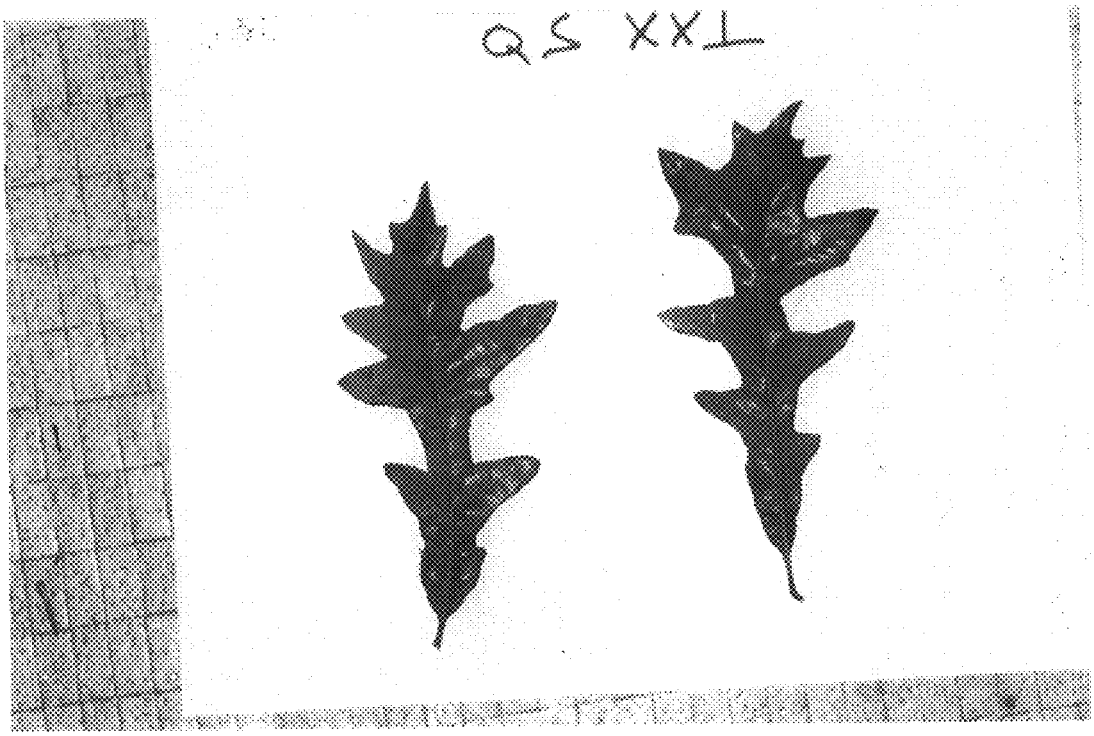
FIG. 5 is a close up of typical fall leaf color of my new variety.

Leaves of my new tree are alternate, simple, typically obovate-oblong in shape, typically about 6 to 8" long, and typically about 1½ to 3" wide, acute or obtuse, cuneate at the base, and deeply lyrate-pinnatified. The upper leaf surface in summer (FIG. 3) is a dark green (RHS 131A), and the lower leaf surface (FIG. 4) is a lighter green (RHS 137C). Fall color (FIG. 5) is typically yellow-orange-red (e.g. RHS 34A).

The buds are typical of the species, being imbricate, ⅛ to ¼" long, and brown with gray-brown, stipular appendages nestled in a cluster of terminal buds.

My new variety has not yet been observed to produce flowers, pollen or acorns.

The root system of my new tree is a very fibrous root system typical of the species.

THE PLANT

Parentage: Discovered as a chance seedling of unkown parentage growing in a cultivated area in Statesboro, Ga.

Tree shape: My new tree is dense and upright with the lower branches being upswept. The branching as a whole displays an upright pyramidal oval in youth.

Trunk: Single leader.

Bark: The bark of my new tree is typical of the species, being smooth to slightly rough and gray-brown on young trees, and becoming gray to gray-green (RHS 188C) and scaly on mature trees, reminiscent of *Quercus alba* with patches of light green-white (RHS 157C).

Braches: Dense, upright uniform branching habit. Branches at the base of the tree typically emerge at about 80 degree angles to the trunk. Branches at the top of the tree typically emerage at about 50 degree angles to the leader. Thus, the branches tend to flatten with age.

Leaves: Leaves are alternate, simple, typically obovate-oblong in shape, typically about 6 to 8" long, typically about 1½ to 3" wide, acute or obtuse, cuneate at the base, and deeply lyrate-pinnatified. Leaves are typically dark green in summer (upper leaf surface RHS 131A, lower leaf surface lighter green, RHS 137C) and yellow-orange-red in the fall (e.g. RHS 34A).

Buds: The buds are typical of the species, being imbricate, ⅛ to ¼" long, and brown with gray-brown, stipular appendages nestled in a cluster of terminal buds.

Pollen and acorns: None observed.

Root system: The root system is typical of the species. Oaks typically have coarse root systems, but Overcup Oak trees have a very fibrous root system as compared to the genus.

Hardiness: Trees being grown in hardiness Zone 7. Winter hardiness not yet determined.

Pest and disease resistance: No unusual pest or disease resistance or susceptibility observed.

I claim:

1. A new and distinct variety of Overcup Oak tree substantially as herein shown and described, characterized particularly as to novelty by its unique dense, upright, uniform branching habit, yellow-orange-red fall color, and fast growth rate.

* * * * *